(12) United States Patent
Pisano et al.

(10) Patent No.: US 8,853,233 B2
(45) Date of Patent: Oct. 7, 2014

(54) BROAD-SPECTRUM ANTI-CANCER TREATMENT BASED ON IMINOCAMPTOTHECIN DERIVATIVES

(75) Inventors: Claudio Pisano, Aprilia (IT); Loredana Vesci, Rome (IT); Franco Zunino, Milan (IT)

(73) Assignees: Sigma-Tau Industrie Farmaceutiche Riunite S.p.A., Rome (IT); Istituto Nazionale per lo Studio e la Cura dei Tumori, Milan (IT)

( * ) Notice: Subject to any disclaimer, the term of this patent is extended or adjusted under 35 U.S.C. 154(b) by 847 days.

(21) Appl. No.: 12/526,225

(22) PCT Filed: Feb. 7, 2008

(86) PCT No.: PCT/EP2008/000928
§ 371 (c)(1),
(2), (4) Date: Sep. 18, 2009

(87) PCT Pub. No.: WO2008/098701
PCT Pub. Date: Aug. 21, 2008

(65) Prior Publication Data
US 2010/0048603 A1   Feb. 25, 2010

(30) Foreign Application Priority Data

Feb. 13, 2007   (EP) .................................... 07102209

(51) Int. Cl.
*A61K 31/4745*   (2006.01)

(52) U.S. Cl.
CPC ................................. *A61K 31/4745* (2013.01)
USPC ......................................................... 514/283

(58) Field of Classification Search
None
See application file for complete search history.

(56) References Cited

U.S. PATENT DOCUMENTS

| 6,242,457 B1 | 6/2001 | Penco et al. |
| 7,888,368 B2 * | 2/2011 | Pisano et al. .................. 514/283 |
| 2008/0033003 A1 | 2/2008 | Dal Pozzo et al. |

FOREIGN PATENT DOCUMENTS

WO   2007/022041 A   2/2007

OTHER PUBLICATIONS

Dallavalle et al. J. Med. Chem., 2001, vol. 44, pp. 3264-3274.*

* cited by examiner

*Primary Examiner* — James D Anderson
(74) *Attorney, Agent, or Firm* — Lucas & Mercanti, LLP

(57) ABSTRACT

A subclass of camptothecin derivatives is disclosed to be useful for the preparation of a medicament for the treatment of a cancer or tumor pathology selected from the group consisting of head and neck carcinoma, pancreas carcinoma, melanoma, bladder carcinoma, mesothelioma and epidermoid skin carcinoma.

3 Claims, No Drawings

BROAD-SPECTRUM ANTI-CANCER TREATMENT BASED ON IMINOCAMPTOTHECIN DERIVATIVES

CROSS-REFERENCE TO RELATED APPLICATION

This application is a 371 of PCT/EP2008/000928 filed on Feb. 7, 2008, which claims the benefit of European Patent Application No. 07102209.9 filed on Feb. 13, 2007, the contents of each of which are incorporated herein by reference.

FIELD OF THE INVENTION

The present invention relates to the use of a subclass of camptothecin derivatives for the preparation of a medicament for the treatment of a cancer or tumor pathology selected from the group consisting of head and neck carcinoma, for example squamous oral, epidermoid submaxillary salivary gland or squamous pharynx carcinoma, pancreas carcinoma, melanoma, bladder carcinoma, mesothelioma, epidermoid skin carcinoma.

BACKGROUND OF THE INVENTION

Camptothecin derivatives are DNA-topoisomerase I inhibitors that have emerged as a prominent class of anticancer agents. Together with the taxanes, the topoisomerase I inhibitors are presumably the most important new class of anticancer drugs introduced into clinical practice. Pre-clinical studies demonstrated significant in vitro and in vivo activity of topoisomerase I inhibitors, such as camptothecin and its derivatives, on a broad range of tumors. The results from clinical trials were promising, as shown by the registration of two topoisomerase inhibitors, topotecan and irinotecan (also known as CPT-11), in many European countries and in the USA, for treatment of patients with ovarian and colorectal cancer, respectively. Other derivatives are currently at different stages of clinical development.

In patent application EP1044977 and in J. Med. Chem. 2001, 44, 3264-3274, camptothecin derivatives are described which bear an alkyloxime O-substituted at position 7 and which are endowed with antitumor activity higher than the compound of reference topotecan. Moreover these camptothecin derivatives bearing an imino group on position 7, also show an improved therapeutic index. Among these compounds one of the preferred molecules was shown to be 7-t-butoxyiminomethylcamptothecin (CPT 184, also known as ST1481 orgimatecan).

One of the main limitations of tumor therapies available today is the resistance of some kind of tumors to chemotherapy treatment (including camptothecin treatment). Moreover, despite of preliminary promising results, it is very difficult to find a drug, which is able to treat successfully different kinds of tumors.

DESCRIPTION OF THE INVENTION

It has now surprisingly found that two camptothecin derivatives have shown a superior efficacy with respect to the reference compound (irinotecan) in terms of tumor volume inhibition (TVI %), log cell kill (LCK), which is a measure of reduction of the tumor size, complete response (CR) or long term survivors (LTS) against a wide spectrum of tumor xenografts in vivo.

Moreover the therapeutic index of these two camptothecin derivatives evaluated in some animal models was higher than that found with irinotecan (2.0 vs 1.0, respectively), suggesting a major tolerability in addition to the high antitumor effect.

In particular the main object of the present invention is the use of a compound of Formula I,

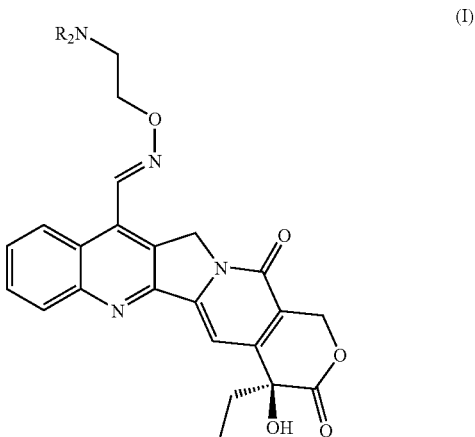

(I)

where R is hydrogen or $C_1$-$C_4$ alkyl, for the preparation of a medicament for the treatment of a cancer or tumor pathology selected from the group consisting of head and neck carcinoma, for example squamous oral, epidermoid submaxillary salivary gland or squamous pharynx carcinoma, pancreas carcinoma, melanoma, bladder carcinoma, mesothelioma and epidermoid skin carcinoma.

Compounds of Formula (I) also comprise tautomers, geometrical isomers, optically active forms as enantiomers, diastereomers and racemate forms, as well as pharmaceutically acceptable salts of the compounds of Formula (I).

Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

Preferably R is hydrogen or methyl.

Preferred compounds of Formula (I) are:
7-(2-amino)ethoxyiminomethylcamptothecin, (ST1968, also known as CPT188) and 7-(2-dimethylamino)ethoxyiminomethylcamptothecin (ST1969).

The compounds of Formula (I) may be prepared from readily available starting materials using the following general methods and procedures. It will be appreciated that where typical or preferred experimental conditions (i.e. reaction temperatures, time, moles of reagents, solvents, etc.) are given, other experimental conditions can also be used, unless otherwise stated. Optimum reaction conditions may vary with the particular reactants or solvents used, but such conditions can be determined by one skilled in the art by routine optimisation procedures. Specific reference is made to the methods described in patent application EP1044977 and in J. Med. Chem. 2001, 44, 3264-3274.

A method of treating a mammal suffering from a cancer or tumor pathology selected from the group consisting of head and neck carcinoma, for example squamous oral, epidermoid submaxillary salivary gland or squamous pharynx carcinoma, pancreas carcinoma, melanoma, bladder carcinoma, mesothelioma, epidermoid skin carcinoma, comprising administering a therapeutically effective amount of a compound of Formula (I) as described above represents one of the aspects of the present invention.

The term "therapeutically effective amount" as used herein refers to an amount of a therapeutic agent needed to treat, ameliorate a targeted disease or condition, or to exhibit a detectable therapeutic effect.

For any compound, the therapeutically effective dose can be estimated initially either in cell culture assays, for example, of neoplastic cells, or in animal models, usually mice or rats.

The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination (s), reaction sensitivities, and tolerance/response to therapy. This amount can be determined by routine experimentation and is within the judgement of the clinician. Generally, an effective dose will be from 0.01 mg/kg to 100 mg/kg, preferably 0.05 mg/kg to 50 mg/kg. Compositions may be administered individually to a patient or may be administered in combination with other agents, drugs or hormones.

The medicament may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra- arterial, intramedullary, intrathecal, intraventricular, transdermal or transcutaneous applications, subcutaneous, intraperitoneal, intranasal, enteral, topical, sublingual, intravaginal, rectal means or locally on the diseased tissue after surgical operation.

Dosage treatment may be a single dose schedule or a multiple dose schedule.

The invention will now be illustrated in greater detail by means of non-limiting Examples.

EXAMPLES

In Vivo Antitumoral Activity on Different Tumor Xenograft Models

ST1968 delivered intravenously showed a wide spectrum of efficacy against different xenograft tumor models. Using a q4dx4 schedule, ST1968 was compared to irinotecan or other known chemotherapeutic agents against head and neck carcinoma (KB squamous oral, A253 epidermoid submaxillary salivary gland, FaDu squamous pharynx), MiaPaCa2 pancreas ca., 501Mel melanoma, HT1376 bladder ca., MESO mesothelioma, A431 epidermoid skin ca.

Methods

Exponentially growing tumor cells were injected s.c. into nude athymic mice. The number of tumor cells was previously chosen by a growth curve. Mice were housed inside cages of makrolon (33.2×15×13 cm) with stainless steel cover-feed and sterilized and dust-free bedding cobs. Animals were housed under a light-dark cycle, keeping temperature and humidity constant. Parameters of the animal rooms were assessed as follows: 22±2° C. temperature, 55±10% relative humidity, about 15-20 filtered air changes/hour and 12 hour circadian cycle of artificial light (7 a.m., 7 p.m.). At request, the environmental conditions were monitored and the data are retained in Animal Housing Archives. Drinking water was supplied ad libitum. Each mouse was offered daily a complete pellet diet (GLP 4RF21, Mucedola) throughout the study. The analytical certificates of animal food and water are retained at Sigma-Tau premises. All animals were weighed before starting the experiment and were subdivided into the different dosage groups. Each cage was identified by a paper tag indicating: cage number, group, date of tumor injection, starting date of treatment, name of the test item, dose and route of administration, date of sacrifice.

Tumor growth was followed by biweekly measurements of tumor diameters with a Vernier caliper. Tumor volume (TV, $mm^3$) was calculated as: [length (mm)×width $(mm)^2$]/2, where the width and the length are the shortest and the longest diameters of each tumor, respectively.

The efficacy of the drug treatment was assessed as: a) Tumor volume inhibition (TVI %) in treated versus control mice, calculated as: 100−[(mean tumor volume of treated animals/mean tumor volume of control animals)×100]; b) LCK ($\log_{10}$ cell kill) calculated by the formula LCK=(T−C)/3.32×DT, where T and C are the mean times (days) required for treated (T) and control (C) tumor, respectively, to reach 1000 $mm^3$, and DT is the doubling time of control tumors; CR meaning no evidence of tumor lasting for at least 10 days. LTS (long term survivors) were considered mice without tumor 90 days upon the tumor injection.

The toxicity of the drug treatments was determined as: body weight loss percent (% BWL max)=100−(mean $BW_{day\,x}$/mean $BW_{day\,1}$×100), where $BW_x$ is the mean BW at the day of maximal loss during the treatment and $BW_1$ is the mean BW on the $1^{st}$ day of treatment.

Therapeutic index was evaluated as ratio between MTD (maximum tolerate dose) and ED80 (efficacious dose) of ST1968.

Results

ST1968 revealed a potent antitumor effect against head and neck (KB, A253, FaDu) and epidermoid skin (A431) tumor xenograft models since it was able to induce a high number of long term survivors (LTS). Compared with the reference compound irinotecan, ST1968 showed to be more efficacious in terms of tumor volume inhibition (TVI %), log cell kill (LCK), complete response (CR) or long term survivors (LTS) against different tumor xenografts (KB, A253, MiaPaca2, HT1376, MeSO, A431). Compared with cisplatin in pharynx tumor bearing mice, ST1968 was more potent for its major persistence of effect on tumor growth upon the end of the treatment (see LCK and LTS). Moreover the therapeutic index of ST1968 evaluated on A253 tumor model was higher than that found with irinotecan (2.0 vs 1.0, respectively), suggesting a major tolerability apart from the high antitumor effect.

TABLE 1

| TUMOR XENOGRAFT | COMPOUND | DOSE (mg/kg) AND ROUTE | SCHEDULE | TVI % | LCK | CR | LTS |
|---|---|---|---|---|---|---|---|
| Squamous oral KB | ST1968 | 35 i.v. | q4d × 4 | 100 | >>4.0 | 7/7 | 7/7 |
| | | 17.5 i.v. | q4d × 4 | 99 | 3.79 | 4/8 | 4/8 |
| | irinotecan | 60 i.v. | q4 d × 4 | 92 | 1.63 | 0/8 | 0/8 |
| | | 30 i.v. | q4d × 4 | 74 | 1.26 | 0/7 | 0/7 |
| Epidermoid submaxillary salivary gland A253 | ST1968 | 35 i.v. | q4d × 4 | 96 | 1.5 | 0/7 | 2/7 |
| | | 30 i.v. | q4d × 4 | 90 | 1.2 | 0/8 | 1/8 |
| | | 15 i.v. | q4d × 4 | 84 | 0.6 | 0/8 | 0/8 |
| | irinotecan | 60 i.v. | q4d × 4 | 79 | 0.5 | 0/8 | 0/8 |
| | | 30 i.v. | q4d × 4 | 33 | 0.1 | 0/8 | 0/8 |
| Squamous pharynx FaDu | ST1968 | 35 i.v. | q4d × 4 | 100 | >>3.9 | 7/7 | 7/7 |
| | | 30 i.v. | q4d × 4 | 100 | >>3.9 | 8/8 | 8/8 |
| | | 15 i.v. | q4d × 4 | 100 | >>3.9 | 8/8 | 8/8 |
| | irinotecan | 60 i.v. | q4d × 4 | 100 | >>3.9 | 8/8 | 8/8 |
| | | 30 i.v. | q4d × 4 | 100 | >>3.9 | 8/8 | 8/8 |
| | cisplatin | 7 i.v. | q7d × 3 | 99 | 3.9 | 1/8 | 3/8 |
| | | 4.7 i.v. | q7d × 3 | 93 | 1.6 | 1/8 | 0/8 |
| Pancreas MiaPaCa2 | ST1968 | 30 i.v. | q4d × 4 | 89 | 1.67 | 0/8 | 0/8 |
| | | 17.5 i.v. | q4d × 4 | 75 | 1.23 | 0/7 | 0/7 |
| | irinotecan | 60 i.v. | q4d × 4 | 69 | 1.23 | 0/7 | 0/7 |
| Melanoma 501Mel | ST1968 | 30 i.v. | q4d × 4 | 68 | 1.4 | 0/10 | 0/10 |
| | | 20 i.v. | q4d × 4 | 65 | 1.0 | 0/6 | 0/6 |
| | irinotecan | 50 i.v. | q4d × 4 | 70 | 1.3 | 0/10 | 0/10 |
| Bladder HT1376 | ST1968 | 30 i.v. | q4d × 4 | 77 | 0.5 | 1/12 | 0/12 |
| | irinotecan | 50 i.v. | q4d × 4 | 46 | 0.2 | 0/10 | 0/10 |
| Mesothelioma MESO | ST1968 | 30 i.v. | q4d × 4 | 92 | 1.4 | 2/12 | 0/12 |
| | irinotecan | 50 i.v. | q4d × 4 | 76 | 0.8 | 0/12 | 0/12 |
| Epidermoid skin A431 | ST1968 | 30 i.v. | q4d × 4 | 100 | >>7.7 | 12/12 | 12/12 |
| | irinotecan | 50 i.v. | q4d × 4 | 100 | 6.8 | 12/12 | 9/12 |

Therapeutic Index as MTD/ED80 on A253: 2.0 for ST1968, 1.0 for irinotecan.

When the number in the column of LCK was defined as >>, it was not possible to calculate a LCK value 90 days after tumor injection because the tumor lesion was completely absent or present only in some of treated mice.

The invention claimed is:

1. Method of treating a mammal suffering from head and neck carcinoma, comprising administering a therapeutically effective amount of 7-(2-amino)ethoxyimino-methylcamptothecin to said mammal, or a pharmaceutical composition containing 7-(2-amino)ethoxyiminomethylcamptothecin, pharmaceutically acceptable carriers and/or excipients.

2. The method of claim 1, wherein the therapeutically effective amount is from 0.01 mg/kg to 100 mg/kg.

3. The method of claim 1, wherein the therapeutically effective amount is from 0.05 mg/kg to 50 mg/kg.

* * * * *